United States Patent
Yates et al.

(10) Patent No.: US 10,014,129 B2
(45) Date of Patent: Jul. 3, 2018

(54) BATTERY DISCONNECTION CIRCUIT

(71) Applicant: SANOFI-AVENTIS DEUTSCHLAND GMBH, Frankfurt am Main (DE)

(72) Inventors: Barry Yates, Kenilworth (GB); Aidan Michael O'Hare, Coventry (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 578 days.

(21) Appl. No.: 14/356,945

(22) PCT Filed: Nov. 15, 2012

(86) PCT No.: PCT/EP2012/072794
§ 371 (c)(1),
(2) Date: May 8, 2014

(87) PCT Pub. No.: WO2013/072444
PCT Pub. Date: May 23, 2013

(65) Prior Publication Data
US 2014/0292108 A1    Oct. 2, 2014

(30) Foreign Application Priority Data
Nov. 18, 2011   (EP) .................................. 11189725

(51) Int. Cl.
*H01H 9/54* (2006.01)
*H01M 2/34* (2006.01)
(Continued)

(52) U.S. Cl.
CPC ................ *H01H 9/54* (2013.01); *A61M 5/20* (2013.01); *A61M 5/24* (2013.01); *H01M 2/34* (2013.01);
(Continued)

(58) Field of Classification Search
CPC ........ H01H 9/54; H01M 10/448; H01M 2/34; H01M 2220/30; H01M 2200/108;
(Continued)

(56) References Cited

U.S. PATENT DOCUMENTS 533,575 A    2/1895 Wilkens
5,226,895 A    7/1993 Harris
(Continued)

FOREIGN PATENT DOCUMENTS

CN    100392964 C    6/2008
EP    0937471    8/1999
(Continued)

OTHER PUBLICATIONS

International Search Report for Int. App. No. PCT/EP2012/072794, completed Nov. 28, 2012.
(Continued)

*Primary Examiner* — Jared Fureman
*Assistant Examiner* — Emmanuel R Dominique
(74) *Attorney, Agent, or Firm* — McCarter & English, LLP

(57) ABSTRACT

The invention is related to an apparatus comprising a switch configured to variably connect a device circuit of an electronic device to a battery, a cutout control circuit connected to the switch and comprising a supply power input and a cutout activation input, wherein the cutout control circuit is configured to turn the switch on when a supply voltage is connected to the supply power input. The invention is further related to a drug delivery device for delivering at least one drug agent comprising an apparatus of the aforementioned kind, a charging connector for a drug delivery device of the aforementioned kind and a method for manufacturing a drug delivery device of the aforementioned kind.

14 Claims, 12 Drawing Sheets

(51) Int. Cl.
*A61M 5/20* (2006.01)
*A61M 5/24* (2006.01)
*H01M 10/44* (2006.01)
A61M 5/19 (2006.01)

(52) U.S. Cl.
CPC ............ *H01M 10/448* (2013.01); *A61M 5/19* (2013.01); *A61M 2205/8212* (2013.01); *A61M 2205/8237* (2013.01); *A61M 2205/8262* (2013.01); *A61M 2207/00* (2013.01); *H01M 2200/108* (2013.01); *H01M 2220/30* (2013.01); Y10T 307/858 (2015.04)

(58) Field of Classification Search
CPC .. A61M 5/24; A61M 5/20; A61M 2205/8237; A61M 2205/8262; A61M 2205/8212; A61M 2207/00; A61M 5/19; Y10T 307/858
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,818,203 A * | 10/1998 | Narita | H01M 10/44 320/128 |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,271,605 B1 * | 8/2001 | Carkner | H02J 7/0031 307/125 |
| 6,329,795 B1 | 12/2001 | Nakashimo | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2003/0172928 A1 * | 9/2003 | Rand | A61M 15/0065 128/203.15 |
| 2004/0059299 A1 | 3/2004 | Moller | |
| 2004/0119341 A1 * | 6/2004 | Hickle | A61M 16/01 307/66 |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0162017 A1 * | 7/2005 | Chin | G06F 1/266 307/44 |
| 2006/0153693 A1 | 7/2006 | Fiechter et al. | |
| 2006/0229521 A1 * | 10/2006 | Barr | A61B 5/0006 600/509 |
| 2007/0191758 A1 * | 8/2007 | Hunter | A61B 17/20 604/22 |
| 2007/0220290 A1 * | 9/2007 | Tsai | G06F 1/266 713/300 |
| 2009/0140184 A1 * | 6/2009 | Crivelli | A61M 5/16881 251/129.01 |
| 2009/0275916 A1 | 11/2009 | Harms et al. | |
| 2010/0259222 A1 | 10/2010 | Senriuchi et al. | |
| 2011/0190693 A1 | 8/2011 | Takatsuka et al. | |

FOREIGN PATENT DOCUMENTS

| | | |
|---|---|---|
| EP | 0937476 | 8/1999 |
| EP | 2186463 | 5/2010 |
| EP | 2335755 | 6/2011 |
| JP | 2011-156005 A | 8/2011 |
| WO | 99/38554 | 8/1999 |
| WO | 01/10484 | 2/2001 |

OTHER PUBLICATIONS

Chinese Office Action for corresponding CN App. No. 201280067316.1, dated Nov. 12, 2015.
Japanese Office Action for JP Application No. 2014-541672, dated Sep. 27, 2016.
European Examination Report for EP Application No. 12784614.5, dated Nov. 9, 2017.

* cited by examiner

BATTERY DISCONNECTION CIRCUIT

CROSS REFERENCE TO RELATED APPLICATIONS

The present application is a U.S. National Phase Application pursuant to 35 U.S.C. § 371 of International Application No. PCT/EP2012/072794 filed Nov. 15, 2012, which claims priority to European Patent Application No. 11189725.2 filed Nov. 18, 2011. The entire disclosure contents of these applications are herewith incorporated by reference into the present application.

TECHNICAL FIELD

The present application relates generally to a battery disconnection circuit, especially to a battery disconnection circuit for a medical device for delivering a medicament.

BACKGROUND

A number of medical devices exist which are purely mechanical, for example injection pens. Other devices already contain electronic parts. However, electronic parts also become part of devices which are so far purely mechanical, for example for allowing easier use, controlling the functions of the device and thus increasing safety, storing information on the usage of the device, and so on.

SUMMARY

There are various devices for delivering one or more drug agents from separate reservoirs. Such drug agents may comprise one or more medicaments. Such a medical device includes a dose setting mechanism for delivering the drug agent(s) automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agent(s) may be contained in one or more multiple dose reservoirs, containers or packages containing independent (single drug compound) or pre-mixed (co-formulated multiple drug compounds) drug agent(s).

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the microcontroller controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The drug delivery device is powered by the electricity provided by a battery. The drug delivery device may comprise a display, a user interface, an electronic control system and one or more motors for driving the injection mechanism. These and other electronic parts or (sub)assemblies require power which can be provided by the battery. In some drug delivery devices, the battery is preassembled within the drug delivery device during production, and the power provided by the battery may be used for testing the produced drug delivery device. After testing is complete, the drug delivery device is turned off but the battery is not removed. One year or more may pass when the drug delivery device is shipped, stored with a distributor, stored on a shelf in retail and bought by a customer before it is finally turned on again. In the meantime, the control circuitry of the drug delivery device may, despite being in a low power state, consume sufficient energy for the battery to reach a state of deep discharge. This is detrimental to the long-term functionality of the battery and may, for example, result in a capacity loss of the battery.

Thus it is an object of the invention to provide a mechanism to reduce the amount of discharged electrical energy of the drug delivery device from production until the time that the drug delivery device is activated by the customer.

This object is solved by an apparatus comprising: a switch configured to variably connect a device circuit of an electronic device to a battery, a cutout control circuit connected to the switch and comprising a supply power input and a cutout activation input, wherein the cutout control circuit is configured to turn the switch on when a supply voltage is connected to the supply power input.

This solution has the further advantage that the number of operations required by the user to prepare the device for first usage is reduced.

The switch provides a defined point at which the device circuit of the drug delivery device is connected to the battery. By using a switch with a low leakage current in the open state and opening the switch after production and factory testing, the drug delivery device may be put in a shelf mode in which less current is discharged from the battery than without the switch. The closed state of the switch corresponds to the state when both poles of the switch are electrically connected, i.e. the switch is turned on. The open state of the switch corresponds to the state when both poles of the switch are electrically disconnected, i.e. the switch is turned off. The drug delivery device is in the shelf mode when the switch is turned off.

The device circuit of the electronic device consists of a main part of the circuitry of the electronic device with the exception of the cutout control circuit. In other words, the device circuit of the electronic device consists of a main part of the circuitry of the electronic device with the exception of the logic controlling the switch. Any parts of the circuit consuming large amounts of current in operation may be separately switched by the control circuit. In particular, the device circuit comprises the circuitry which controls the entirety of the device's operation once the drug delivery device has been connected to a charger for the first time by the user. In the following, the device circuit is denoted as the operational circuitry of the electronic device.

The switch may be an electrical switch, an electronic switch, for example a transistor, or a mechanical switch. The switch may comprise a micro-fuse. The switch may be a two-pole switch.

The battery may in particular be a rechargeable battery, for example a NiMH (nickel-metal hydride) battery, a lithium-ion battery, a lithium-polymer battery or the like. The only logic circuitry that will still need to be supplied with battery power is the cutout control circuit which closes the switch once the connection to an external supply voltage is detected. Since the cutout control circuit performs only few functions, it may be implemented in a way which will deplete significantly less energy from the battery than the operational circuitry when it is connected to the battery.

The detection of an external supply voltage indicates that the drug delivery device has been connected to an external charger, from which it follows that the drug delivery device has been received by a customer and has entered operation, thereby signaling that the shelf mode can be left.

A preferred embodiment is characterized in that the cutout control circuit is configured to turn the switch off when an activation signal is detected at the cutout activation input.

The activation signal may be a voltage level corresponding either to a high voltage or a low voltage. In particular, the high voltage level may correspond to the voltage level of the supply voltage of the electronic device, whereas the low voltage level may correspond to the voltage level of the ground node of the electronic device. Thus, the high voltage level may for example be 5 V and the low voltage level may be 0V.

The activation signal may also be a command received from a communication interface. This command may be an analog or a digital signal and may be communicated serially or in parallel.

Another preferred embodiment is characterized in that the cutout activation input is controlled by the device circuit, wherein the cutout control circuit is configured to turn the switch off when a corresponding control command is received by the device circuit. This way the shelf mode can be activated internally without the need for an external activation signal.

A preferred embodiment is characterized in that the cutout control circuit is configured to supply charging power to the battery from the supply power input. By having the electricity for charging the battery being funneled through the cutout control circuit, a simple and effective mechanism for detecting the connection to an external charger within the cutout control circuit may be implemented.

A further preferred embodiment is characterized in that a first contact of the switch is connected to the battery.

Another preferred embodiment is characterized in that a second contact of the switch is connected to a supply voltage node of the device circuit of the electronic device, which electronic device is a drug delivery device for delivering at least one drug agent.

A further preferred embodiment is characterized in that the switch is an electronic switch.

A yet further preferred embodiment is characterized in that the switch is a transistor. In particular, the transistor may be a transistor with an especially low leakage current.

A preferred embodiment is characterized in that the apparatus comprises a motor powered by the battery, wherein the switch is arranged such that the battery is electrically connected to a motor power supply of the motor when the switch is turned on and the battery is electrically connected to the motor power supply of the motor when the switch is turned off. The motor may be an electrical motor. The motor may in particular be configured to propel fluid from the first cartridge or a second cartridge, for example by moving a stopper that moves in the respective cartridge.

Having the battery electrically connected to the motor power supply means that power is available to the motor.

A further preferred embodiment is characterized in that the apparatus further comprises an independent device module and comprises an independent power supply switch configured to variably connect the independent device module to the battery, wherein the device circuit is configured to control the independent motor power supply switch.

The independent device module may be a circuit or some other component requiring power, such as a motor. The independent device module may be any component advantageously switched separately from the device circuit consisting of the main part of the circuitry.

For the exemplary case that the independent device module is a motor, by this embodiment a further switch is included as part of the motor power supply, controlled by the circuitry which controls the entirety of the device's operation. The motor power supply is therefore disconnected from the battery in shelf mode since the circuitry which controls the entirety of the device's operation is not powered and therefore the motor power supply is not connected to the battery.

By having the battery be electrically connected to the motor power supply via the separate switch controlled by the circuitry which controls the entirety of the device's operation, the significant current drawn by the motor flows through a single switch instead of two switches, reducing the voltage drop owing to the switch resistance.

Another preferred embodiment is characterized in that the apparatus further comprises an external port with a plurality of pins, wherein a power supply pin of the plurality of pins is electrically connected to the supply power input. The external port may be a port configured to receive a connector, in particular a charger connector. Likewise, the connector is configured to connect to the port. The external port may for example be a USB port. Any or all pins of the external port may in turn be contacted by corresponding contacts of the connector.

Any further pins of the plurality of pins beside the power supply pin may be connected to further respective inputs of either the cutout control circuit or of the device circuit. The power supply pin may be configured to provide an electrical connection to the battery or a battery charging circuit via the supply power input to charge the battery of the drug delivery device. Not every pin of the plurality of pins needs to be configured to be contacted by a corresponding pin of the connector.

In yet another preferred embodiment the plurality of pins comprises a cutout activation pin, which cutout activation pin is electrically connected to the cutout activation input. By having a pin in the external port which is electrically connected to the cutout activation input, it becomes possible to apply a desired voltage level to the cutout activation input via the cutout activation pin. Thus, the shelf mode can be activated by means of a connector connected with the external port. It may be that the connector of a charger for use by the customer is configured not to connect to the cutout activation pin of the external port, whereas a factory connector only used in production and testing is in fact configured to connect to the cutout activation pin. Thereby the shelf mode can only be activated by the factory connector but not by the connector of the charger.

In yet a further preferred embodiment, the external port is configured to receive a charging connector, which charging connector comprises at least two contacts and wherein the cutout activation pin is electrically isolated from at least one contact of the charging connector. Thereby it is prevented that the shelf mode is falsely entered by means of some signal transmitted through the charging connector connected to the external port. Such a situation may occur either when there is an electrical malfunction, i.e. the charging connector has irregular voltage levels which inadvertently cause the device to enter shelf mode. In this case, the customer may think the device malfunctioning and return it for service. It may also occur when third parties somehow learn of this shelf mode functionality and deliberately try to hack the device by applying the shelf-mode signal themselves through the charging connector.

However, there may be a different type of connector, for example a factory connector, also configured to connect to the external port and comprising a contact configured to electrically connect to the cutout activation pin, thereby enabling the activation of the shelf mode by means of a signal transmitted through this different type of connector.

In an example embodiment, there is provided a drug delivery device for delivering at least one drug agent comprising an apparatus according to the invention, wherein a total power consumption of the drug delivery device when the switch is turned off is determined based on a power consumption of the cutout control circuit.

This may mean that the total power consumption of the drug delivery device when the switch is turned off is substantially equal to the power consumption of the cutout control circuit. In other words, when the switch is turned off, there is no other component of the drug delivery device that consumes a non-negligible amount of power.

It may also mean that the total power consumption of the drug delivery device when the switch is turned off is substantially equal to the power consumption of the cutout control circuit plus another substantially constant power consumption. This may for example be the case for the example embodiment comprising the motor power supply switch, in which the total power consumption of the drug delivery device when the switch is turned off is substantially equal to the power consumption of the cutout control circuit plus the power consumption of the motor power supply switch.

The power which is consumed is provided by the battery of the drug delivery device. Thereby turning the switch off and thus entering the shelf mode reduces the total power consumption of the drug delivery device to the power consumption of the cutout control circuit, which is very low due to the simplicity and relatively small size (in terms of chip size or number of components) of the cutout control circuit and the selection of these components for low power consumption.

It may also be that the total power consumption of the drug delivery device when the switch is turned off is equal to the power consumption of the cutout control circuit. This means that, when the switch is turned off, there is no other component of the drug delivery device that consumes any battery power except for (unwanted) leakage currents.

The object of the invention is further solved by a charging connector for a drug delivery device for delivering at least one drug agent, which drug delivery device comprises an apparatus according to the invention, which charging connector is configured to connect to the external port of the drug delivery device, configured to supply charging power to the power supply pin and configured to transmit a cutout activation signal to the cutout activation input. The charging power may be supplied as DC power. The charging connector may be part of a charger configured to be connected to an AC voltage socket. The charger may further comprise a transformer or switch mode power supply for transforming the AC voltage level from the AC voltage socket to a voltage level suitable for charging. The charger may further comprise a rectifier for transforming the AC voltage to a DC voltage for charging the drug delivery device via the power supply pin.

The object of the invention is further solved by a method for manufacturing a drug delivery device for delivering at least one drug agent, comprising assembling a circuitry module of the drug delivery device, the circuitry module comprising a battery, a device circuit for controlling the delivery of the at least one drug, a cutout control circuit for controlling the voltage supply of the device circuit, a switch configured to be controlled by the cutout control circuit and to variably connect the battery to the device circuit, connecting the battery to the device circuit by closing the switch, testing the functionality of the drug delivery device, disconnecting the battery from the device circuit by opening the switch.

The circuitry module and the elements it comprises may be assembled in any order. After the circuitry module is assembled with the elements it comprises, the switch is closed, thereby supplying the device circuit with power from the battery and rendering both the device circuit and the drug delivery device as a whole operational. When the switch has been closed and power is supplied, the drug delivery device may be tested. This production test may comprise a simulation of real operations—for example testing the operation of the drug delivery device under simulated user input to the user interface—as well as test routines which may use a dedicated test interface. For example, a dedicated test routine may run on a microcontroller of the drug delivery device and may further output test results of the dedicated test routine. The microcontroller may in particular be part of the device circuit. After completion of the test, the switch is opened, thereby cutting power from the device circuit and putting the drug delivery device into the shelf mode. This may in particular be done by applying an active level voltage at the cutout activation input of the cutout control circuit, either by directly contacting the cutout activation input of the cutout control circuit or via a cutout activation pin of the external port of the drug delivery device.

In another preferred embodiment disconnecting the battery from the device circuit by opening the switch comprises applying an activation signal to a cutout input of the cutout control circuit.

BRIEF DESCRIPTION OF THE FIGURES

These as well as other advantages of various aspects of the present invention will become apparent to those of ordinary skill in the art by reading the following detailed description, with appropriate reference to the accompanying drawings, in which.

DETAILED DESCRIPTION

Figure 1:
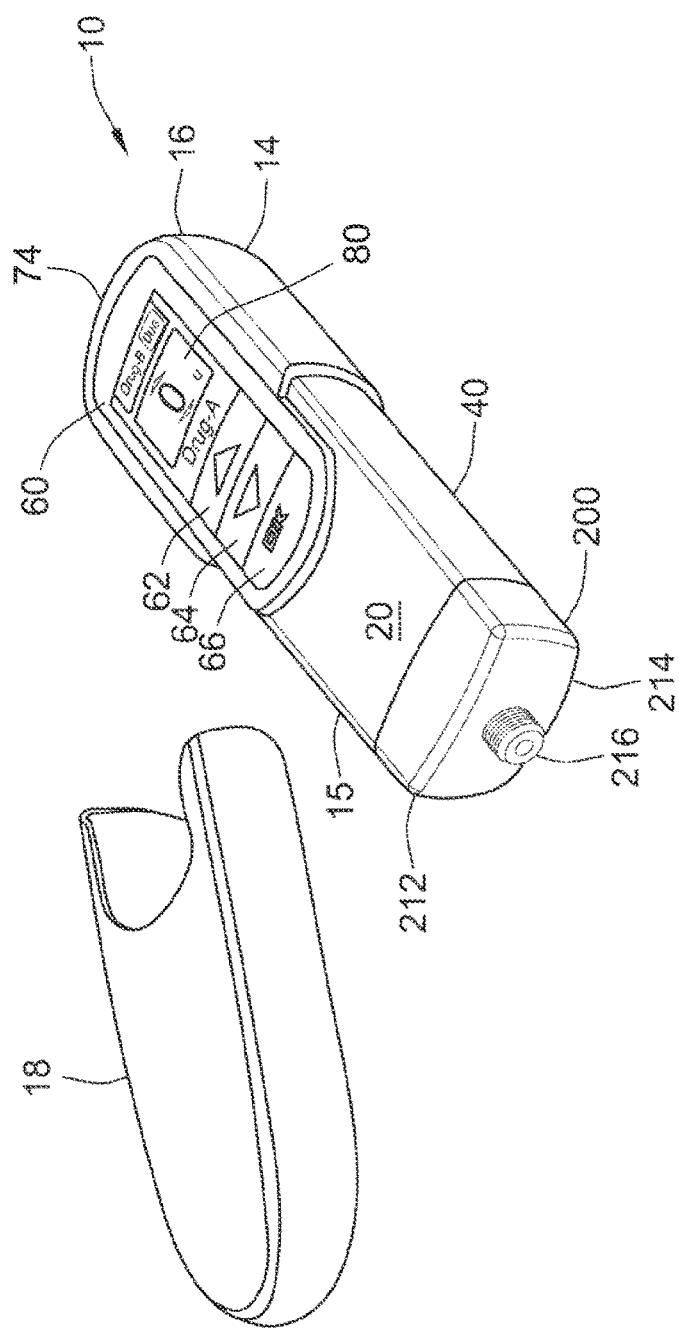
FIG. 1 illustrates a perspective view of a delivery device with an end cap of the device removed.
Figure 2:
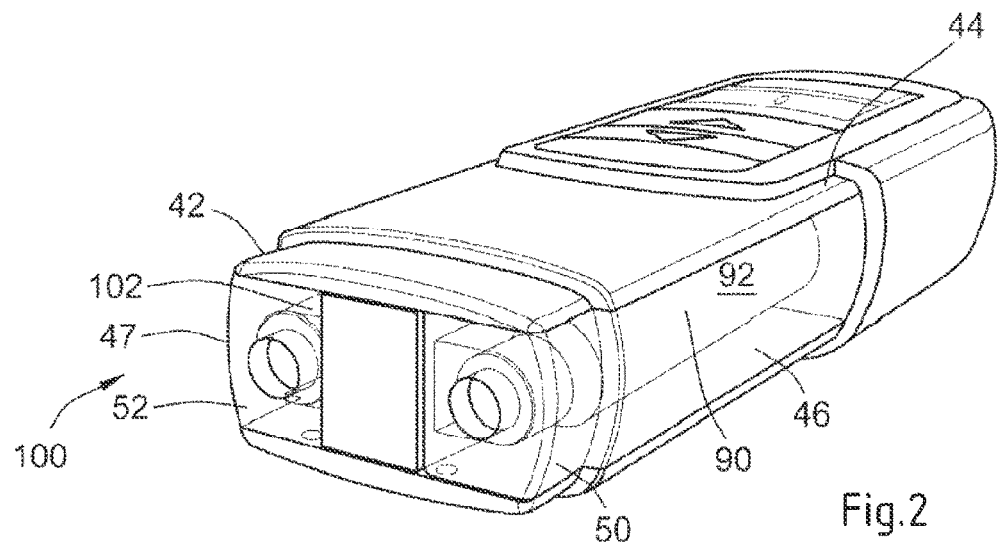
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a microcontroller control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
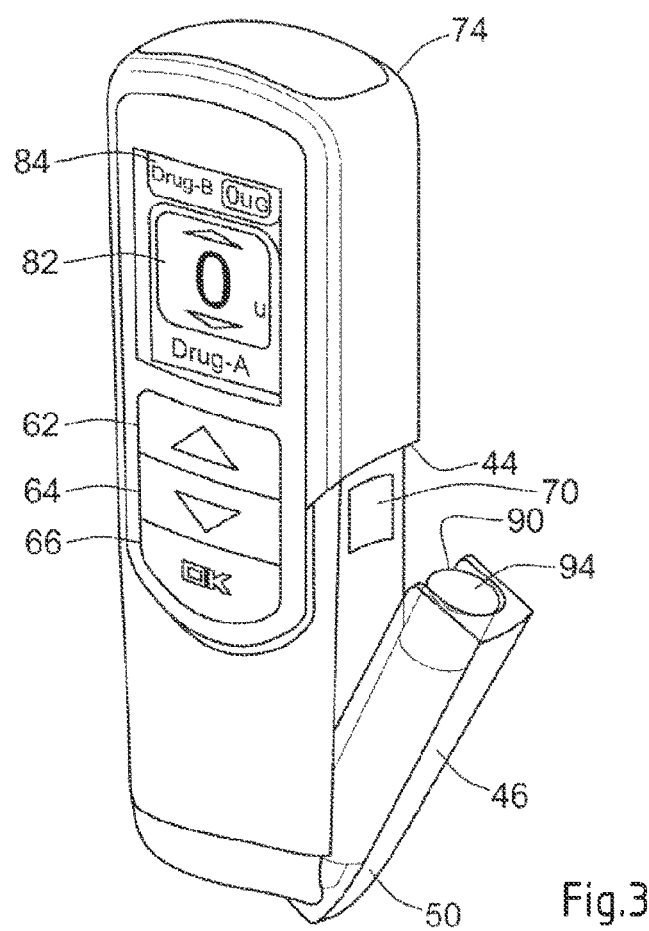
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
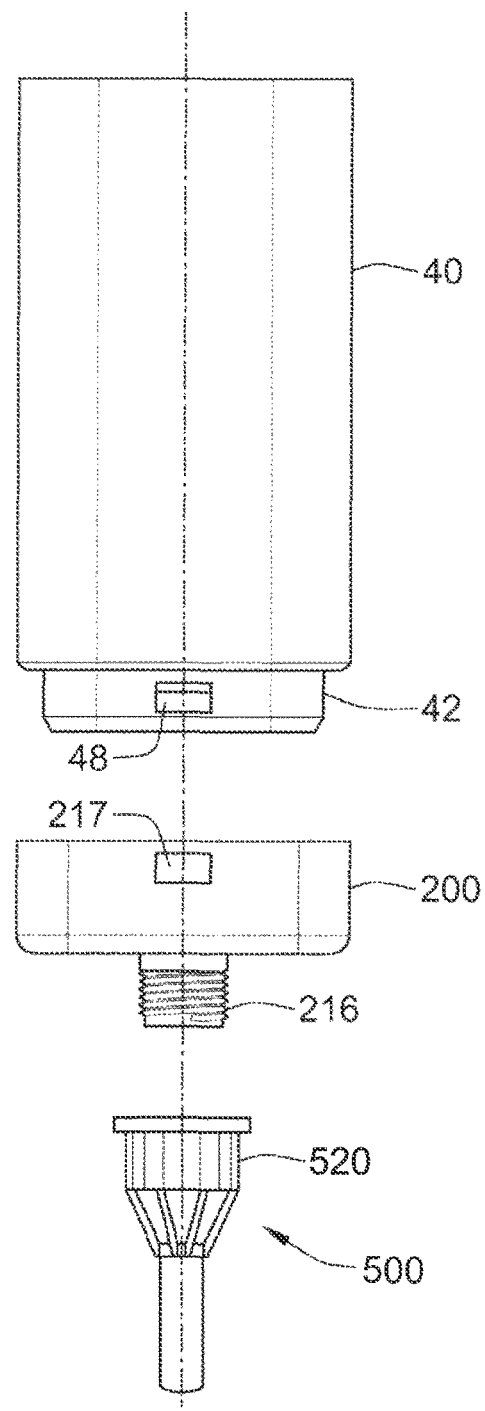
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
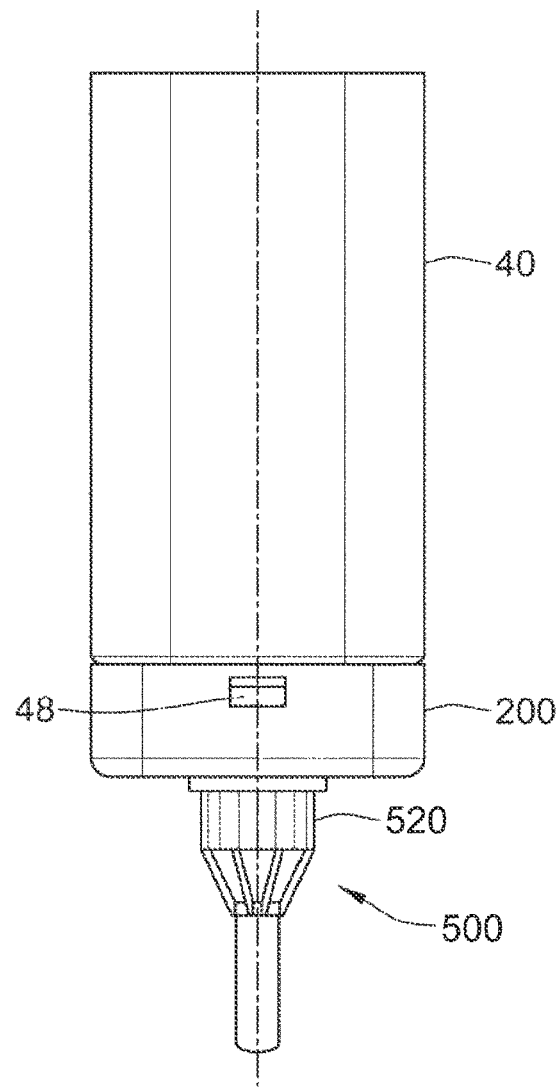
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
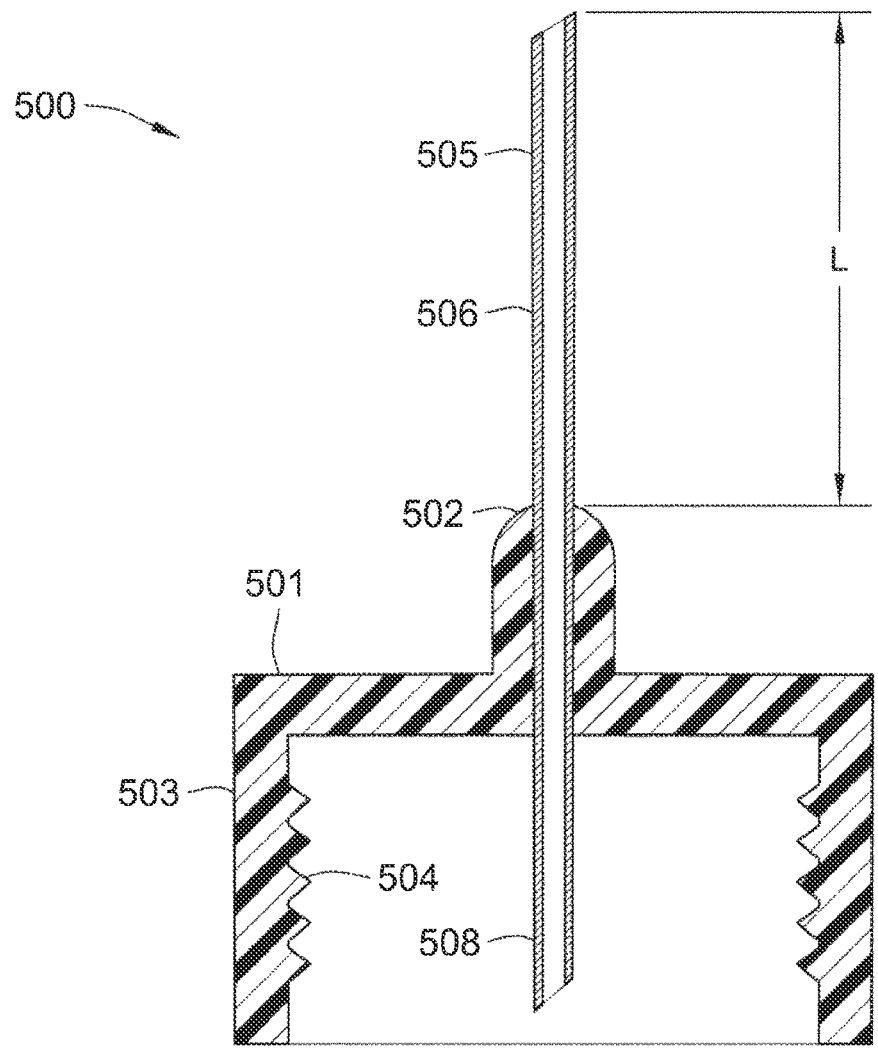
FIG. 6 illustrates one arrangement of a needle assembly that may be mounted on a distal end of the delivery device.
Figure 7:
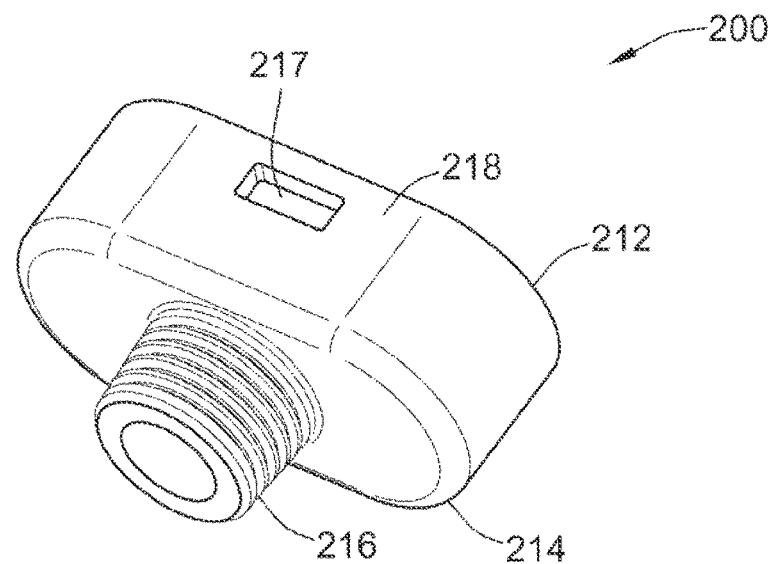
FIG. 7 illustrates a perspective view of the dispense interface illustrated in FIG. 4.

FIG. 5 also illustrates the needle assembly 500 and protective cover 420 coupled to the distal end of the dispense interface 200 that may be screwed onto the needle hub of the interface 200. FIG. 6 illustrates a cross sectional view of the double ended needle assembly 502 mounted on the dispense interface 200 in FIG. 5.

The needle assembly 500 illustrated in FIG. 6 comprises a double ended needle 506 and a hub 501. The double ended needle or cannula 506 is fixedly mounted in a needle hub 501. This needle hub 501 comprises a circular disk shaped element which has along its periphery a circumferential depending sleeve 503. Along an inner wall of this hub member 501, a thread 504 is provided. This thread 504 allows the needle hub 501 to be screwed onto the dispense interface 200 which, in one preferred arrangement, is provided with a corresponding outer thread along a distal hub. At a center portion of the hub element 501 there is provided a protrusion 502. This protrusion 502 projects from the hub in an opposite direction of the sleeve member. A double ended needle 506 is mounted centrally through the protrusion 502 and the needle hub 501. This double ended needle 506 is mounted such that a first or distal piercing end 505 of the double ended needle forms an injecting part for piercing an injection site (e.g., the skin of a user).

Similarly, a second or proximal piercing end 508 of the needle assembly 500 protrudes from an opposite side of the circular disc so that it is concentrically surrounded by the sleeve 503. In one needle assembly arrangement, the second or proximal piercing end 508 may be shorter than the sleeve 503 so that this sleeve to some extent protects the pointed end of the back sleeve. The needle cover cap 520 illustrated in FIGS. 4 and 5 provides a form fit around the outer surface 503 of the hub 501.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 500 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
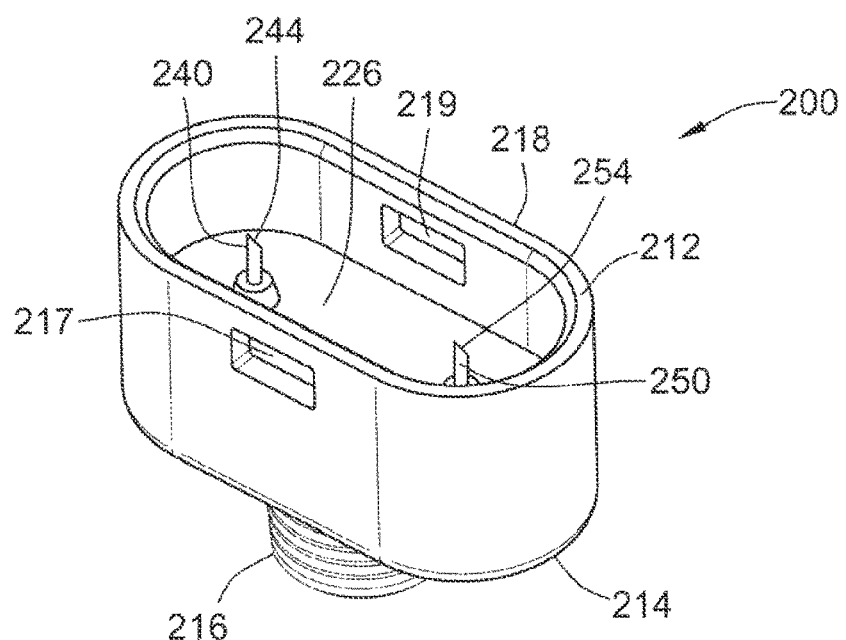
FIG. 8 illustrates another perspective view of the dispense interface illustrated in FIG. 4.
Figure 9:
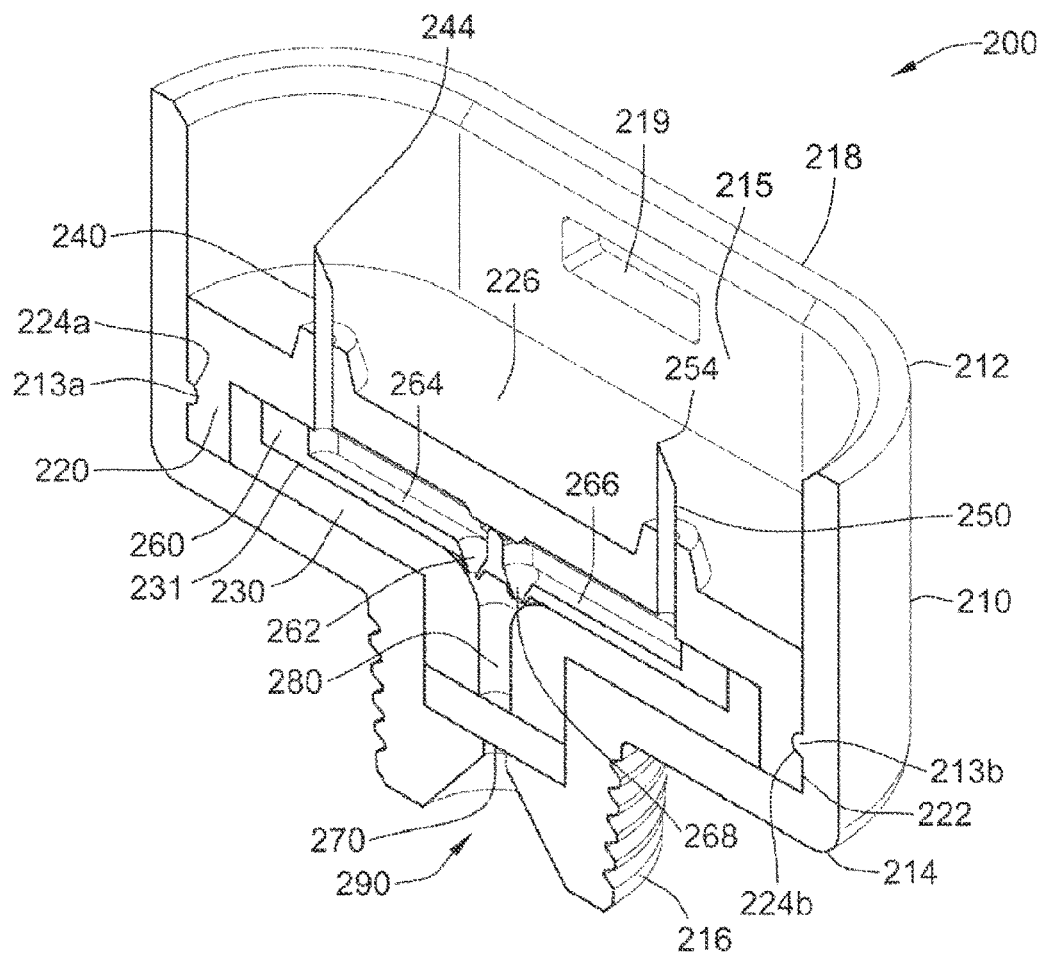
FIG. 9 illustrates a cross-sectional view of the dispense interface illustrated in FIG. 4.
Figure 10:
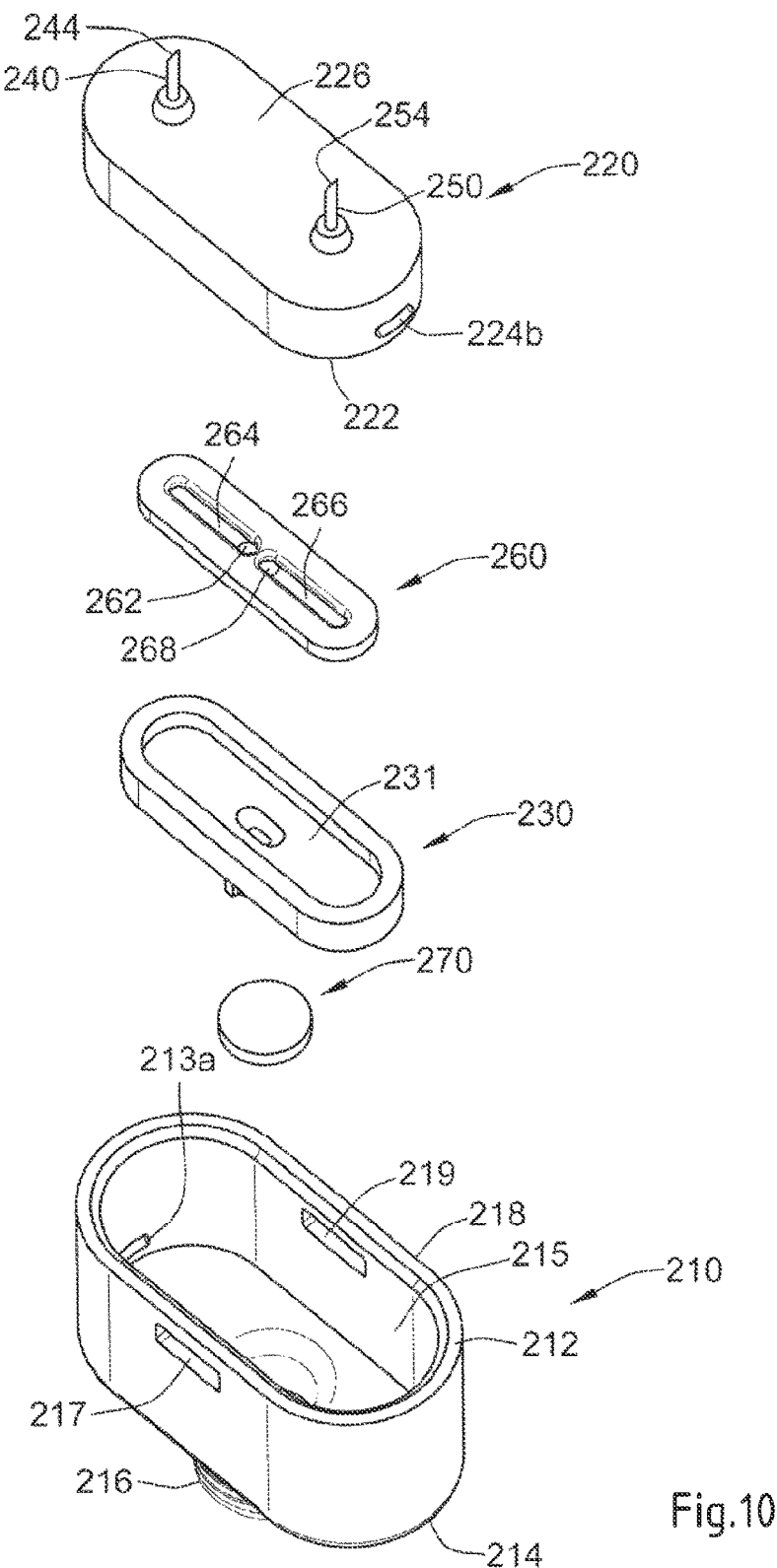
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
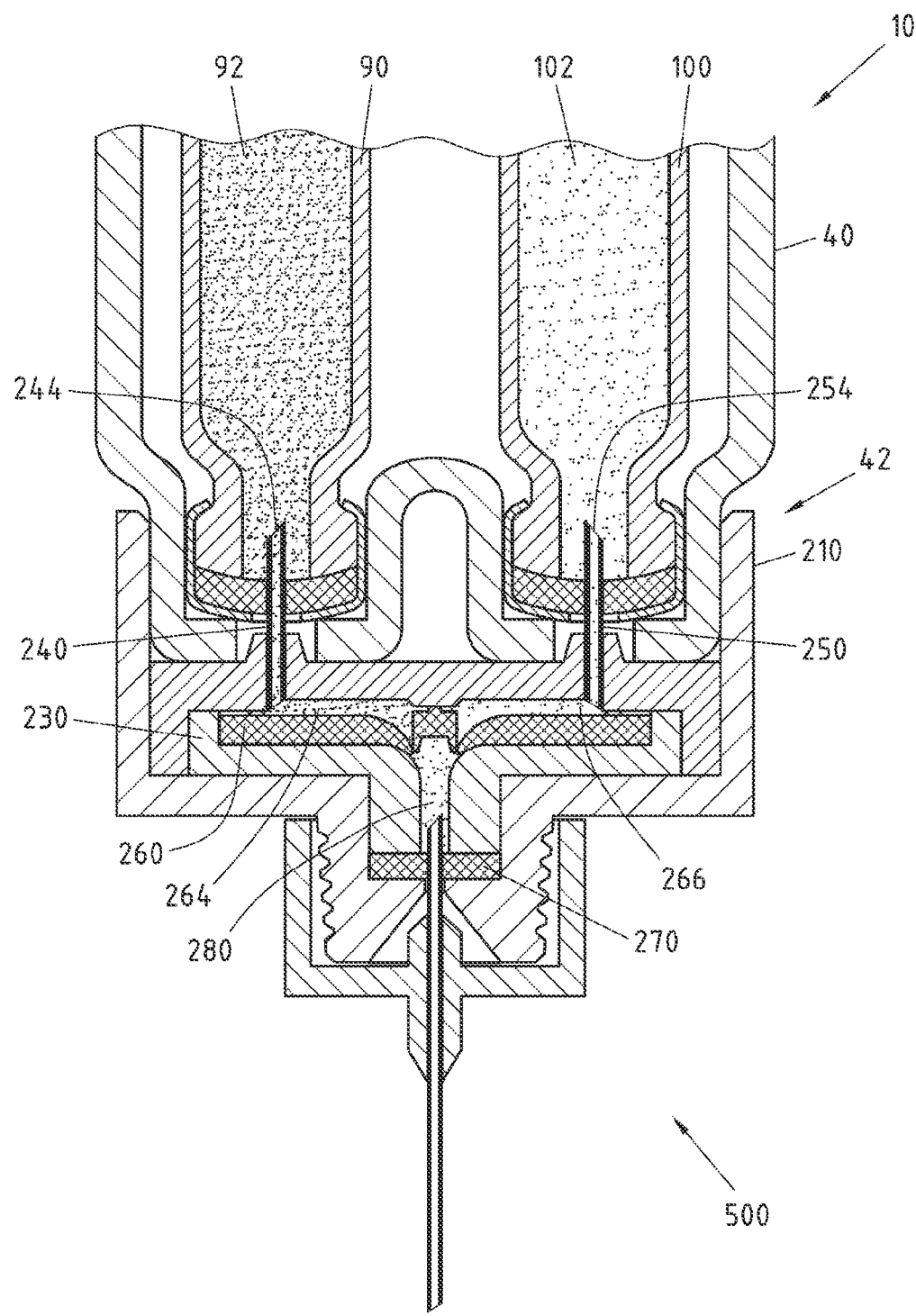
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 500 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 500. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
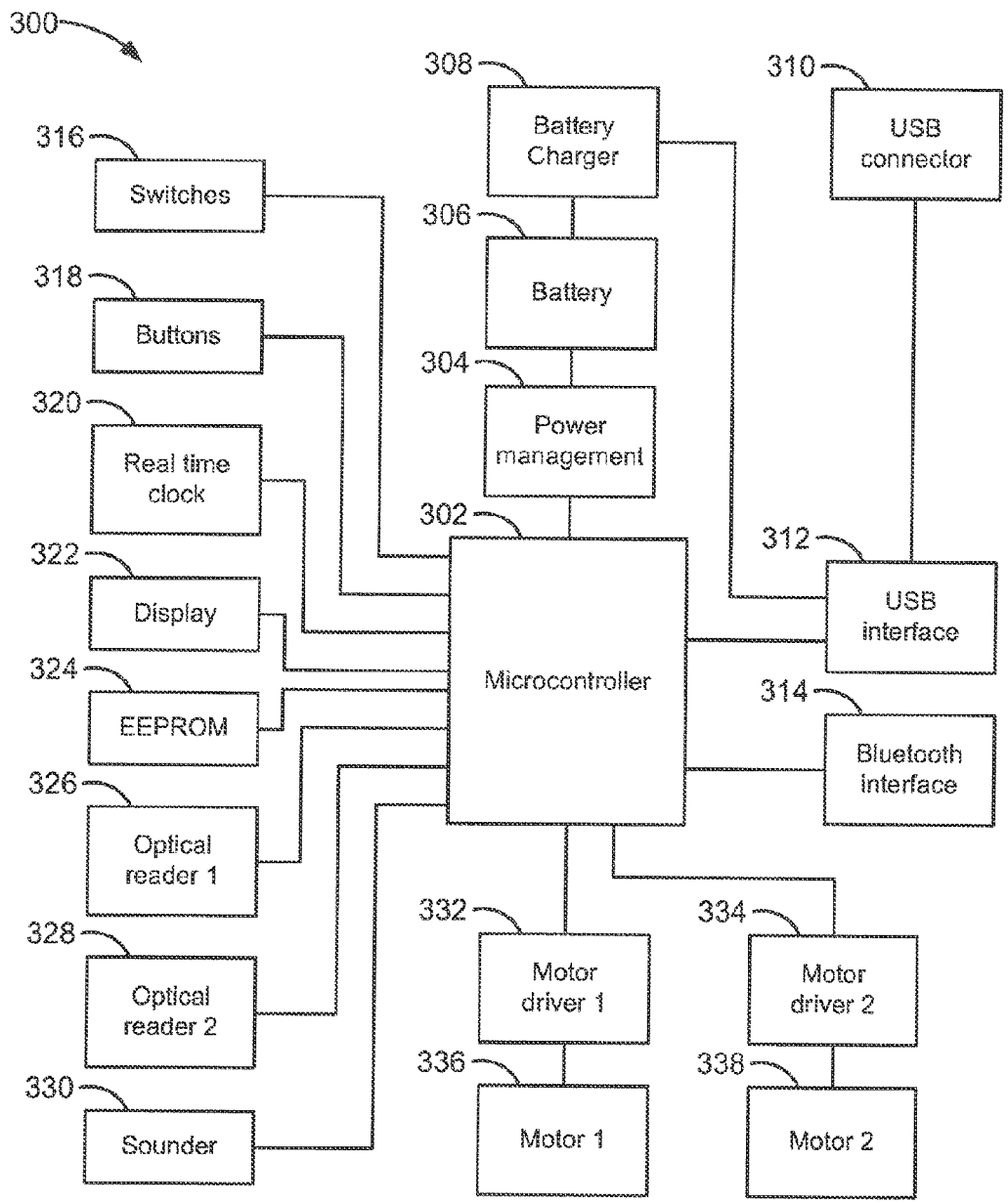
FIG. 12 illustrates a block diagram functional description of a control unit for operation of the drug delivery device illustrated in FIG. 4.
Figure 13:
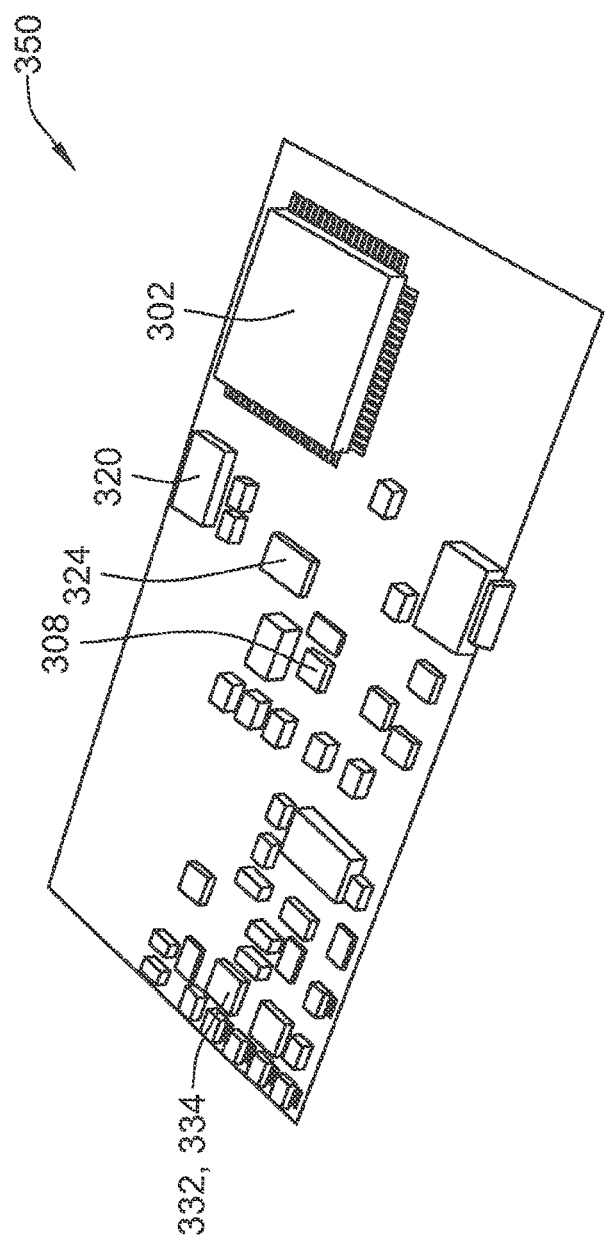
FIG. 13 illustrates a printed circuit board assembly of the drug delivery device illustrated in FIG. 4.

FIG. 12 illustrates a functional block diagram of a control unit to operate and control the drug delivery device illustrated in FIG. 1. FIG. 13 illustrates one arrangement of a printed circuit board (PCB) or printed circuit board assembly (PCBA) 350 that may comprise certain portions of the control unit illustrated in FIG. 12.

Referring now to both FIGS. 12 and 13, it may be seen that the control unit 300 comprises a microcontroller 302. Such a microcontroller may comprise a Freescale MCF51JM microcontroller. The microcontroller is used to control the electronic system for the drug delivery device 10. It includes internal analogue to digital converters and general purpose digital I/O lines. It can output digital Pulse Width Modulated (PWM) signals. It includes an internal USB module. In one arrangement, a USB protection circuit such as ON-Semi NUP3115 may be implemented. In such an implementation, the actual USB communications may be provided on board the microcontroller 302.

The control unit further comprises a power management module 304 coupled to the microcontroller 302 and other circuit elements. The power management module 304 receives a supply voltage from a main power source such as the battery 306 and regulates this supply voltage to a plurality of voltages required by other circuit components of the control unit 300. In one preferred control unit arrangement, switched mode regulation (by means of a National Semiconductor LM2735 is used to step up the battery voltage to 6V, with linear regulation to generate other supply voltages required by the control unit 300.

The battery 306 provides power to the control unit 300 and is preferably supplied by a single lithium-ion or lithium-polymer cell. This cell may be encapsulated in a battery pack that contains safety circuitry to protect against overheating, overcharging and excessive discharge. The battery pack may also optionally contain coulomb counting technology to obtain an improved estimate of remaining battery charge.

A battery charger 308 may be coupled to the battery 306. One such battery charger may be based on a Freescale Semiconductor MC34674 or MC34675 along with other supporting software and hardware modules. As an alternative, a Texas Instruments (TI) BQ24150 may be used. In one preferred arrangement, the battery charger 308 takes energy from the external wired connection to the drug delivery device 10 and uses it to charge the battery 306. The battery charger 308 can also be used to monitor the battery voltage and charge current to control battery charging. The battery charger 308 can also be configured to have bidirectional communications with the microcontroller 302 over a serial bus. The charge status of the battery 306 may be communicated to the microcontroller 302 as well. The charge current of the battery charger may also be set by the microcontroller 302.

The control unit may also comprise a USB connector 310. A micro USB-AB connector or a custom design of connector may be used for wired communications and to supply power to the device.

The control unit may also comprise a USB interface 312. This interface 312 may be external to the microcontroller 302. The USB interface 312 may have USB master and/or USB device capability. The USB interface 312 may also provide USB on-the-go functionality. The USB interface 312 external to the microcontroller also provides transient voltage suppression on the data lines and VBUS line.

In an alternative embodiment, an external Bluetooth interface 314 may also be provided. The Bluetooth interface 314 is preferably external to the microcontroller 302 and communicates with this controller 302 using a data interface.

Preferably, the control unit further comprises a plurality of switches 316. In the illustrated arrangement, the control unit 300 may comprise eight switches 316 and these switches may be distributed around the device. These switches 316 may be used to detect and or confirm at least the following:

a. Whether the dispense interface 200 has been properly attached to the drug delivery device 10;
b. Whether the removable cap 18 has been properly attached to the main body 20 of the drug delivery device 10;
c. Whether the first cartridge retainer 50 of the cartridge holder 40 for the first cartridge 90 has been properly closed;
d. Whether the second cartridge retainer 52 of the cartridge holder 40 for the second cartridge 100 has been properly closed;
e. To detect the presence of the first cartridge 90;
f. To detect the presence of the second cartridge 100;
g. To determine the position of the stopper 94 in the first cartridge 90; and
h. To determine the position of the stopper 104 in the second cartridge 100.

These switches 316 are connected to digital inputs, for example to general purpose digital inputs, on the microcontroller 302. Preferably, these digital inputs may be multiplexed in order to reduce the number of input lines required. Interrupt lines may also be used appropriately on the microcontroller 302 so as to ensure timely response to changes in switch status.

In addition, and as described in greater detail above, the control unit may also be operatively coupled to a plurality of human interface elements or push buttons 318. In one preferred arrangement, the control unit 300 comprises eight push buttons 318 and these are used on the device for user input for the following functions:

a. Dose dial up;
b. Dose dial down;
c. Sound level;
d. Dose;
e. Eject;
f. Prime;
g. Back; and
h. OK.

These buttons 318 are connected to digital inputs, for example to general purpose digital inputs, on the microcontroller. Again, these digital inputs may be multiplexed so as to reduce the number of input lines required. Interrupt lines will be used appropriately on the microcontroller to ensure timely response to changes in switch status. In an example embodiment, the function of one or more buttons may be replaced by a touch screen.

In another example embodiment, not each of the 8 buttons need to be present. For example, priming may be done by the "dose"-button, and the "prime"-button may therefore not be present.

In one version, the control unit 300 comprises a real time clock 320. Such a real time clock may comprise an Epson RX4045 SA. The real-time clock 320 may communicate with the microcontroller 302 using a serial peripheral interface or similar.

In an alternative version, the real time clock is contained within one of the microcontrollers.

A digital display module 322 in the device preferably uses LCD or OLED technology and provides a visual signal to the user. The display module incorporates the display itself and a display driver integrated circuit. This circuit communicates with the microcontroller 302 using a serial peripheral interface or parallel bus.

The control unit 300 also comprises a memory device, for example volatile and non-volatile memory. Volatile memory may be random access memory (RAM), for example static RAM or dynamic RAM and/or the like, as working memory of microcontroller 302. Non-volatile memory may be read only memory (ROM), FLASH memory or electrically erasable programmable read-only memory (EEPROM), such as an EEPROM 324. Such an EEPROM may comprise an ON Semiconductor CAT25128. As an alternative, an Atmel AT25640 may be used. The EEPROM may be used to store system parameters and history data. This memory device 324 communicates with the processor 302 using a serial peripheral interface bus.

In an alternative embodiment, the control unit 300 further comprises a first and a second optical reader 326, 328. Such optical readers may comprise Avago ADNS3550. These optical readers 326, 328 may be optional for the drug delivery device 10 and are, as described above, used to read information from a cartridge when such a cartridge is inserted into either the first or the second cartridge retainers 50, 52. Preferably, a first optical reader is dedicated for the first cartridge and the second optical reader is dedicated for the second cartridge. An integrated circuit designed for use in optical computer mice may be used to illuminate a static 2D barcode on the drug cartridge, positioned using a mechanical feature on the drug cartridge, and read the data it contains. This integrated circuit may communicate with the microcontroller 302 using a serial peripheral interface bus. Such a circuit may be activated and deactivated by the microcontroller 302 e.g., to reduce power consumption when the circuit is not needed, for example by extinguishing the cartridge illumination when data is not being read.

As previously mentioned, a sounder 330 may also be provided in the drug delivery device 10. Such a sounder may comprise a Star Micronics MZT03A. Applicants' proposed sounder may be used to provide an audible signal to the user. The sounder 330 may be driven by a pulse-width modulation (PWM) output from the microcontroller 302. In an alternative configuration, the sounder may play polyphonic tones or jingles and play stored voice commands and prompts to assist the user in operating or retrieving information from the device.

The control unit 300 further comprises a first motor driver 332 and a second motor driver 334. The motor drive circuitry may comprise Freescale MPC17533 and is controlled by the microcontroller 302. For example, where the motor drive comprises a stepper motor drive, the drive may be controlled using general purpose digital outputs. Alternatively, where the motor drive comprises a brushless DC motor drive, the drive may be controlled using a Pulse Width Modulated (PWM) digital output. These signals control a power stage, which switches current through the motor windings. The power stage requires continuous electrical commutation. This may for example increase device safety, decreasing the probability of erroneous drug delivery.

The power stage may consist of a dual H-bridge per stepper motor, or three half-bridges per brushless DC motor. These may be implemented using either discrete semiconductor parts or monolithic integrated circuits.

The control unit 300 further comprises a first and a second motor 336, 338, respectively. As explained in greater detail below, the first motor 336 may be used to move the stopper 94 in the first cartridge 90. Similarly, the second motor 338 may be used to move the stopper 104 in the second cartridge. The motors can be stepper motors, brushless DC motors, or any other type of electric motor. The type of motor may determine the type of motor drive circuit used. The electronics for the device may be implemented with one main, rigid printed circuit board assembly, potentially with additional smaller flexible sections as required, e.g., for connection to motor windings and switches.

The microcontroller provided on the PCBA 350 will be programmed to provide a number of features and carry out a number of calculations. For example, and perhaps most importantly, the microcontroller will be programmed with an algorithm for using a certain therapeutic dose profile to calculate at least a dose of the secondary medicament based at least in part on the selected dose of the primary medicament.

For such a calculation, the controller may also analyze other variables or dosing characteristics in calculating the amount of second medicament to administer. For example, other considerations could include at least one or more of the following characteristics or factors:

a. Time since last dose;
b. Size of last dose;
c. Size of current dose;
d. Current blood glucose level;
e. Blood glucose history;
f. Maximum and/or minimum permissible dose size;
g. Time of day;
h. Patient's state of health;
i. Exercise taken; and
j. Food intake.

These parameters may also be used to calculate the size of both the first and the second dose size.

In one arrangement, and as will be described in greater detail below, a plurality of different therapeutic dose profiles may be stored in the memory device or devices operatively coupled to the microcontroller. In an alternative arrangement, only a single therapeutic dose profile is stored in the memory device operatively coupled to the microcontroller.

The presently proposed electromechanical drug delivery device is of particular benefit to patients with dexterity or computational difficulties. With such a programmable device, the single input and associated stored predefined therapeutic profile removes the need for the user or patient to calculate their prescribed dose every time they use the device. In addition, the single input allows easier dose setting and dispensing of the combined compounds.

In addition to computing the dose of the second medicament, the microcontroller can be programmed to achieve a number of other device control operations. For example, the microcontroller may be programmed so as to monitor the device and shut down the various elements of the system to save electrical energy when the device is not in use. In addition, the controller can be programmed to monitor the amount of electrical energy remaining in the battery 306. In one preferred arrangement, an amount of charge remaining in the battery can be indicated on the digital display 80 and a warning may be given to the user when the amount of remaining battery charge reaches a predetermined threshold level. In addition, the device may include a mechanism for determining whether there is sufficient power available in the battery 306 to deliver the next dose, or it will automatically prevent that dose from being dispensed. For example, such a monitoring circuit may check the battery voltage under different load conditions to predict the likelihood of the dose being completed. In a preferred configuration the motor in an energized (but not moving) condition and a not energized condition may be used to determine or estimate the charge of the battery.

Preferably, the drug delivery device 10 is configured to communicate via a data link (i.e., either wirelessly or hard wired) with various computing devices, such as a desktop or laptop computer. For example, the device may comprise a Universal Serial Bus (USB) for communicating with a PC or other devices. Such a data link may provide a number of advantages. For example, such a data link may be used to allow certain dose history information to be interrogated by a user. Such a data link could also be used by a health care professional to modify certain key dose setting parameters such as maximum and minimum doses, a certain therapeutic profile, etc. The device may also comprise a wireless data link, for example an IRDA data link or a Bluetooth data link. In an alternative embodiment, a preferred Bluetooth module comprises a Cambridge Silicon Radio (CSR) Blue core 6.

In an example embodiment, the device has USB On-The-Go (USB OTG) capability. USB OTG may allow the drug delivery device 10 to generally fulfill the role of being slave to a USB host (e.g., to a desktop or notebook computer) and to become the host themselves when paired with another slave device (e.g. a BGM).

For example, standard USB uses a master/slave architecture. A USB Host acts as the protocol master, and a USB 'Device' acts as the slave. Only the Host can schedule the configuration and data transfers over the link. The Devices cannot initiate data transfers, they only respond to requests given by a host. Use of OTG in Applicants' drug delivery device 10 introduces the concept that the drug delivery device can switch between the master and slave roles. With USB OTG, Applicants' device 10 at one time be a 'Host' (acting as the link master) and a 'Peripheral' (acting as the link slave) at another time.

Figure 14:
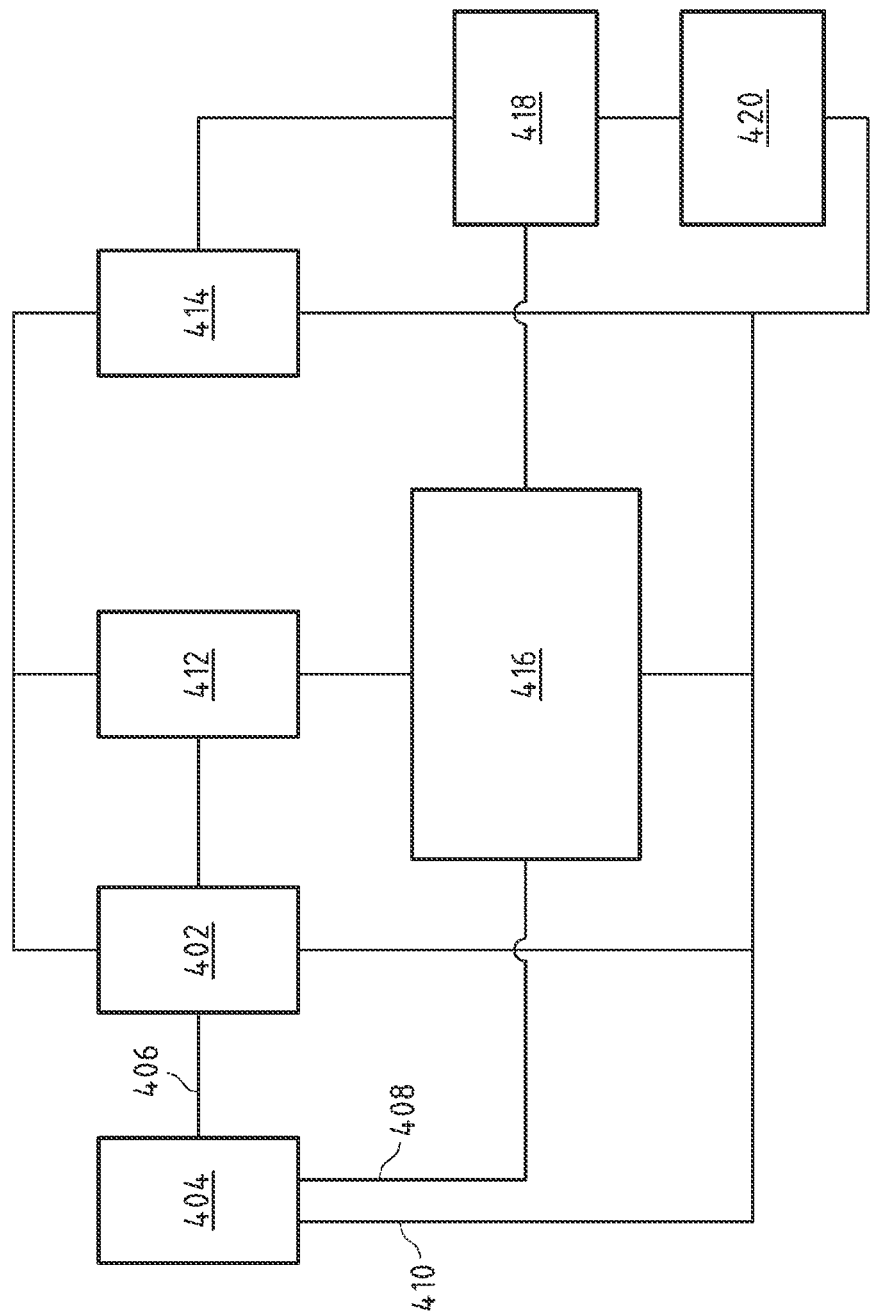
FIG. 14 illustrates a block diagram of an exemplary apparatus according to the invention.

With reference to FIG. 14, there is illustrated an apparatus for switching a battery connection for a drug delivery device as illustrated in FIG. 1. The control unit of the drug delivery device referred to with regard to FIG. 14 corresponds to that illustrated in FIG. 12 unless noted otherwise. Likewise, the printed circuit board assembly of the drug delivery device referred to with regard to FIG. 14 corresponds to that illustrated in FIG. 13 unless noted otherwise.

On the printed circuit board of the drug delivery device, a cutout control circuit 402 is connected to an external port 404. The external port 404 may for example be a data port with additional power supply lines, for example a serial data power, such as a USB port. The port may in particular be a custom connector, for example permitting serial data communication.

The cutout control circuit 402 is comprised in the power management module 304. The external port 404 comprises two data pins, a power in pin, a ground pin and a battery cutout activation pin. The external port 404 is configured to receive a connector. This connector may be the connector of a charger for the drug delivery device but may also be the connector for a factory tester for the drug delivery device. The charger may connect to different pins of the connector than the factory tester.

The power in pin and the battery cutout activation pin are connected to a pair of signal lines 406 comprising a power in line and a cutout activation signal line. The power in line is connected to a supply power input of the cutout control circuit 402 and the cutout activation signal line is connected to a cutout activation input of the cutout control circuit 402.

Both data pins are connected to data signal lines 408 which in turn connect to the device circuit 416, which comprises the microcontroller 302, the other components of the power management module 304 as well as the remaining electronic components of the drug delivery device.

Further the ground pin is connected to a ground line 410 which in turn connects to a ground node of the device circuit 416.

The cutout control circuit 402 is connected to a rechargeable battery 414 of the drug delivery device. This battery may be the battery 306 illustrated in FIG. 12. By this connection, the cutout control circuit 402 on the one hand receives its supply voltage when it does not receive power from the port 404 via the power in line. On the other hand, the cutout control circuit is configured to supply power to the battery 414 and/or to the battery charger, thereby enabling a charging of the battery 414 from the power supplied by a charger connected to the port 404.

Moreover, the cutout control circuit 402 is connected to a transistor switch 412, the switching action of which the cutout control circuit 402 controls. The transistor switch 412 connects the battery 414 with a supply voltage node of the device circuit 416. When the transistor switch 412 is turned on, the device circuit 416 is supplied with power in the form of DC supply voltage from the battery 414. When the transistor switch 412 is turned off, the device circuit 416 is, in effect, electrically disconnected from the battery 414. The only current flowing through the transistor switch 412 is the leakage current. The transistor switch is chosen to have only a minimal leakage current.

There may be one or more sections of the device circuit, which could be denoted in their entirety as an independent device module 420 and may for example consist of a motor, which draw significant current but which are required to be switched, under control of the device circuit 416. In this case, they may have a separate switch, such as an independent power supply switch 418, connected directly to the battery 414 and controlled by the device circuit 416, with the switching arrangement such that they will be disconnected from the battery 414 by the independent power supply switch 418 if the device circuit 416 is disconnected from the battery. Connecting the independent power supply switch 418 directly to the battery reduces the peak current flowing through the main switch 412, relaxing its technical specification and reducing the voltage drop across this switch owing to its resistance in the conducting state. There may also be more than one independent device module 420, each with its own dedicated independent power supply switch 418.

The cutout control circuit 402 is always connected to the battery 414. Therefore, when the transistor switch 412 is turned off, the power drained from the battery 414 will consist of only the power drained from the cutout control circuit 402 and the power corresponding to the leakage current of the transistor switch 412, plus the power corresponding to the leakage current of any independent power supply switches 418 connecting independent device modules 420 which draw significant current. Because the cutout control circuit 402 only implements a very simple functionality, as will be described in the following, the average power consumption of the cutout control circuit 402 is very low.

After assembly of the drug delivery device, and in particular of the PCBA 350 of the drug delivery device, the functionality of the drug delivery device is tested.

This testing procedure also comprises an electronic test as follows. At this point, the battery 414 is charged and the transistor switch 412 is turned on, thereby supplying the device circuit 416 with power and enabling full functionality. A dedicated factory connector is connected to the port 404. The factory connector connects to all pins of the port 404. Via the data pins and the data signal lines 408, an external test control unit communicates with the device circuit 416. As part of this communication, various test information is sent to the device circuit 416, which proceeds to run the tests. The tests are both internal, i.e. testing components within the device circuit 416 as well as external in that they pertain to components outside the device circuit 416 proper, such as for example the display 322 and the sounder 330. The results of these tests are also received back via the data pins and the data signal lines 408 and then further transmitted to the external test control unit via the port 404.

After completion of the test, the drug delivery device is turned into the shelf mode. To this end, an active voltage level of 5V is applied to the cutout activation pin of the external port 404 and via the cutout activation signal line also applied to the cutout activation input of the cutout control circuit 402. Having received this signal, the cutout control circuit 402 turns the transistor switch 412 off, thereby disconnecting the device circuit 416 from the battery 414. The cutout activation circuit 402, as well as other components which do not draw significant amounts of electrical power in their inactive state, such as the motors 336, 338, remains connected to the battery 414. This state is the shelf mode of the drug delivery device, in which essentially only the cutout activation circuit 402 draws current from the battery 414.

The factory connector is now removed from the external port 404. The drug delivery device is packaged, shipped to a distributor, stored there, shipped to a retail store and remains on a shelf there until it is bought by a consumer. This period of time from production to delivery to the customer is called shelf time, though not all of it is technically spent on a shelf. The shelf time may amount to a year. Because the device circuit 426 is effectively disconnected from the battery 414 in that time, only little current is dissipated from the battery 414, essentially consisting only of the leakage current of the transistor switch 412, any additional independent power supply switches 418 and the power consumption of the cutout control circuit 402, which is also low because the cutout control circuit 402 does not need to perform any switching actions in the shelf time.

The shelf mode is ended when the customer inserts a charging connector to the external port 404. The charging connector comprises a contact for the power in pin, with which a charging supply voltage is provided. The charging voltage is provided to the power supply input of the cutout control circuit 402 via the power in line of the pair of signal lines 406. When the supply voltage is detected at the supply power input of the cutout control circuit 402, the cutout control circuit 402 turns the transistor switch 412, thereby providing power both from the supply power input and from the battery to the device circuit 416. The supply voltage from the supply power input is further also provided to the battery 414 and to the battery charger.

The charging connector has no corresponding contact for the cutout activation pin. Consequently, the charging connector cannot re-activate the shelf mode. Thereby the transistor switch 412 remains turned on and the device circuit 416 is continually supplied with power from the battery 414. Re-activation of the shelf mode is not necessary because it is not expected that the drug delivery device will remain inactive for longer periods of time in its operational lifetime.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 0 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus comprising:
    a switch configured to variably connect a device circuit of an electronic device to a battery;
    an external port comprising a power supply pin and a cutout activation pin, wherein the external port is configured to be removably connected to a charging connector, which charging connector comprises at least two contacts, and wherein the cutout activation pin is electrically isolated from at least one contact of the charging connector when the charging connector is received by the external port;
    a power in line and a cutout activation signal line; and
    a cutout control circuit connected to the switch and comprising a supply power input and a cutout activation input,
    wherein the power in line electrically connects the power supply pin and the supply power input,
    wherein the cutout activation signal line electrically connects the cutout activation pin and the cutout activation input, and
    wherein the cutout control circuit is configured to turn the switch on when a supply voltage is connected to the supply power input.

2. The apparatus of claim 1, wherein the cutout control circuit is configured to turn the switch off when an activation signal is detected at the cutout activation input.

3. The apparatus of claim 1, wherein the cutout activation input is controlled by the device circuit, and wherein the cutout control circuit is configured to turn the switch off when a corresponding control command is received by the device circuit.

4. The apparatus of claim 1, wherein the cutout control circuit is configured to supply charging power to the battery from the supply power input.

5. The apparatus of claim 1, wherein a first contact of the switch is connected to the battery.

6. The apparatus of claim 5, wherein a second contact of the switch is connected to a supply voltage node of the device circuit of the electronic device, which electronic device is a drug delivery device for delivering at least one drug agent.

7. The apparatus of claim 1, wherein the switch is an electronic switch.

8. The apparatus of claim 1, wherein the switch is a transistor.

9. The apparatus of claim 1, further comprising a motor powered by the battery, wherein the switch is arranged such that the battery is electrically connected to a motor power supply of the motor when the switch is turned on and the battery is electrically connected to the motor power supply of the motor when the switch is turned off.

10. The apparatus of claim 1, further comprising an independent device module and comprising an independent power supply switch configured to variably connect the independent device module to the battery, wherein the device circuit is configured to control the independent power supply switch.

11. Charging connector for a drug delivery device for delivering at least one drug agents, which drug delivery device comprises an apparatus according to claim 1, configured to connect to the external port of the drug delivery device, configured to supply charging power to the power supply pin and configured to transmit a cutout activation signal to the cutout activation pin.

12. Drug delivery device for delivering at least one drug agent comprising an apparatus according to claim 1, wherein a total power consumption of the drug delivery device when the switch is turned off is determined based on a power consumption of the cutout control circuit.

13. A method for manufacturing a drug delivery device for delivering at least one drug agent, comprising:
    assembling a circuitry module of the drug delivery device, the circuitry module comprising:
        a battery, an external port comprising a power supply pin and a cutout activation pin, wherein the external port is configured to be removably connected to a charging connector, which charging connector comprises at least two contacts, and wherein the cutout activation pin is electrically isolated from at least one contact of the charging connector when the charging connector is received by the external port, a power in line and a cutout activation signal line, a device circuit, a cutout control circuit, wherein the cutout control circuit comprises a supply power input and a cutout activation input, wherein the power in line electrically connects the power supply pin and the supply power input, and wherein the cutout activation signal line electrically connects the cutout activation pin and the cutout activation input, and a switch configured to be controlled by the cutout control circuit and to variably connect the battery to the device circuit;

connecting the battery to the device circuit by closing the switch;

testing the functionality of the drug delivery device; and disconnecting the battery from the device circuit by opening the switch.

14. The method of claim 13, wherein disconnecting the battery from the device circuit by opening the switch comprises applying an activation signal to a cutout input of the cutout control circuit.

* * * * *